(12) United States Patent
Granata et al.

(10) Patent No.: US 7,439,267 B2
(45) Date of Patent: Oct. 21, 2008

(54) ESSENTIAL N-3 FATTY ACIDS IN CARDIAC INSUFFICIENCY AND HEART FAILURE THERAPY

(75) Inventors: Francesco Granata, Milan (IT); Franco Pamparana, Milan (IT); Eduardo Stragliotto, Milan (IT)

(73) Assignee: Pfizer Italia S.R.L., Latina (IT)

( * ) Notice: Subject to any disclaimer, the term of this patent is extended or adjusted under 35 U.S.C. 154(b) by 0 days.

(21) Appl. No.: 11/333,387

(22) Filed: Jan. 17, 2006

(65) Prior Publication Data

US 2006/0205814 A1 Sep. 14, 2006

Related U.S. Application Data

(63) Continuation of application No. 10/451,623, filed as application No. PCT/EP02/00507 on Jan. 16, 2002, now abandoned.

(30) Foreign Application Priority Data

Jan. 25, 2001 (IT) .......................... MI2001A0129

(51) Int. Cl.
*A61K 31/22* (2006.01)
*A61K 31/20* (2006.01)
(52) U.S. Cl. ...................... 514/549; 514/560
(58) Field of Classification Search ............... 514/549, 514/560
See application file for complete search history.

(56) References Cited

U.S. PATENT DOCUMENTS

| 5,502,077 | A | * | 3/1996 | Breivik et al. ............... 514/560 |
| 5,760,081 | A | | 6/1998 | Leaf et al. |
| 6,140,304 | A | | 10/2000 | Sears |

FOREIGN PATENT DOCUMENTS

| CA | 2291959 | | 6/2001 |
| CN | 1082909 | A | 3/1994 |
| DE | 273852 | A1 | 11/1989 |
| DE | 10056351 | | 5/2002 |
| EP | 0 292 846 | A2 | 11/1988 |
| EP | 0 780 124 | B1 | 12/2001 |
| EP | 0 760 393 | B1 | 6/2003 |
| EP | 1 157 692 | B1 | 10/2005 |
| GB | 2090529 | A | 7/1982 |
| GB | 2 221 843 | | 2/1990 |
| IT | 1274734 | | 7/1997 |
| JP | 4182426 | A | 6/1992 |
| JP | 8053350 | | 2/1996 |
| JP | 8151334 | | 6/1996 |
| JP | 2001-247457 | A | 9/2001 |
| WO | WO 87/03899 | A1 | 7/1987 |
| WO | WO 94/20092 | | 9/1994 |
| WO | WO 96/31457 | | 10/1996 |
| WO | WO 96/34846 | A1 | 11/1996 |
| WO | WO 96/34855 | A1 | 11/1996 |
| WO | WO 00/48592 | A1 | 8/2000 |
| WO | WO 01/03696 | A1 | 1/2001 |
| WO | WO 01/36369 | A1 | 5/2001 |
| WO | WO 01/52822 | A1 | 7/2001 |
| WO | WO 01/60778 | A2 | 8/2001 |
| WO | WO 01/76568 | A2 | 10/2001 |
| WO | WO 02/02105 | A1 | 1/2002 |

OTHER PUBLICATIONS

Hazra et al., "Pharmacology and Therapeutic Potential of the n-3 Polyunsaturated Fatty Acids, Eicosapentaenoic Acid (EPA) and Docosahexaenoic acid (DHA) in Fish Oils", Indian Journal of Pharmacology, 1999; 31:247-264.*

British National Formulary, No. 8, 1989, Chapter 2: Cardiovascular System, British Medical Association and the Royal Pharmaceutical Society of Britain.

Burr, et al., "Effects on Changes in Fat, Fish, and Fibre Intakes on Death and Myocardial Reinfarction: Diet and Reinfarction Trial (DART)", The Lancet, 1989:757-761.

Burr, et al., "Diet and Reinfarction Trial (DART): Design, Recruitment, and Compliance", European Heart Journal, vol. 10, 1989:558-567.

Luley, et al., "Bioavailability of Omega-3 Fatty Acids: Ethylester Preparations are as Suitable as Triglyceride Preparations", Akt. Ernähr.—Med., vol. 15, 1990:123-125.

Norday, et al., "Absorption of the n-3 Eicosapentaenoic and Docosahexaenoic Acids as Ethyl Esters and Triglycerides by Humans1-3", Am J Clin Nutr, vol. 53, 1991:1185-1190.

Schmidt, et al., "n-3 Fatty Acids: Prevention and Treatment in Vascular Disease", Bi & Gi Publishers, Springer Verlag, London, 1995.

Singh, et al., "Randomized, Double-Blind, Placebo-Controlled Trial of Fish Oil and Mustard Oil in Patients with Suspected Acute Myocardial Infarction: The Indian Experiment of Infarct Survival—4", Cardiovascular Drugs and Therapy, vol. 11, 1997:485-491.

(Continued)

*Primary Examiner*—Raymond J Henley, III
(74) *Attorney, Agent, or Firm*—Arent Fox LLP

(57) ABSTRACT

The present invention concerns a method of therapeutic prevention and treatment of a heart disease chosen from cardiac insufficiency and heart failure including the administration of an essential fatty acid containing a mixture of eicosapentaenoic acid ethyl ester (EPA) and docosahexaenoic acid ethyl ester (DHA), either alone or in combination with another therapeutic agent.

14 Claims, No Drawings

OTHER PUBLICATIONS

GISSI-Prevenzione Investigators, "Dietary Supplementation with N-3 Polyunsaturated Fatty Acids and Vitamin E After Myocardial Infarction: Results of the GISSI-Prevenzione Trial", The Lancet, vol. 354, 1999:447-455.

Marchioli, et al., "The Results of the GISSI-Prevenzione trial in the General Framework of Secondary Prevention", European Heart Journal, vol. 21, Issue 12, 2000:949-952.

R. Marchioli, "Treatment with n-3 Polyunsaturated Fatty Acids After Myocardial Infarction: Results of GISSI-Prevenzione Trial", European Heart Journal Supplements, vol. 3, (Suppl. D), 2001:D85-D97.

Zarain-Herzberg, et al., "Transcriptional Modulators Targeted at Fuel Metabolism of Hypertrophied Heart", Am. J. Cardiology, 1999; 83:31H-37H.

McCarty, "Fish Oil and Other Nutritional Adjuvants for Treatment of Congestive Heart Failure," Medical Hypothesis, 46, 1996, p. 400-406.

"Effects of long-term fenofibrate therapy on cardiovascular events in 9795 people with type 2 diabetes mellitus (the FIELD study) randomised controlled trial," Articles, 140, 2005, pp. 1-13.

Major Cardiovascular Events in Hypertensive Patients Randomized to Doxazosin vs Chlorthalidone, JAMA, 283(15), 2000, pp. 1967-1975.

S. Takeo, et al., "Effects of long-term treatment with eicosapentaenoic acid on the heart subjected to ischemia/reperfusion and hypoxia/reoxygenation in rats", Molecular and Cellular Biochemistry, vol. 188(1-2), Nov. 1998: pp. 199-208.

Gualler, Eliseo et al: "Omega-3 fatty acids in adipose tissue and risk of myocardial infarction: the EURAMIC study" Arteriosclerosis, Thrombosis, and Vascular Biology (1999), 19 (4), pp. 1111-1118.

Rissanen Tiina et al: "Fish oil-derived fatty acids, docosahexanoic acid and docosapentaenoic acid, and the risk of acute coronary events: The Kupio Ishaemic Heart Disease Risk Factor Study." CIRCULATION, vol. 102, No. 22, Nov. 28, 2000 (2000-11-28), pp. 2677-2679.

Rissanen T H (Reprint) et al: "Fish oil derived fatty acids, docasahexanoic acid and docosapentaenoic acid and the risk of acute myocardial infarction"CIRCULATION, (Oct. 27, 1998) vol. 98, No. 17, Supp. Äsü, pp. 2823-2823.

McCarty,M.F., "Fish Oil and Other Nutritional Adjuvants for Treatment of Congestive Heart Failure," Medical Hypotheses, 1996 vol. 46, pp. 400-406.

L.M. Freeman, et al., "Nutritional alterations and the effect of fish oil supplementation in dogs with heart failure", Journal of veterinary internal medicine/American College of veterinary Internal Medicine, vol. 12(6), Dec. 1998: pp. 440-448.

M.A. Silver, et al., "Difficult cases in heart failure: Cardiac cachexia in advanced heart failure: Suppression of tumour necrosis factor by omega-3 fatty acids", Congestive Heart failure, vol. 4 (5), Nov. 1998: pp. 44-45.

Milani et al., "Can Pharmacologic Modulation of Tumor Necrosis Factor α in Advanced Heart Failure with Cachexia Result in Anabolic Effects?,"J. Heart and Lung Transplant. 15, S85, Abstract 185, 1996.

Toyofuku, Study on protection of ischemic myocardium and arrest of ventricular arrhythmia by omega-3 polyunsaturated fatty acid intake, Jpn. Cir. J., 58, 99. 903-912, 1994.

Kinoshita I. et al., "Antiarrhythmic Effects of Eicosapentaenoic Acid During Myocardial Infarction." Jpn. J. Clin. Physiol., 26, pp. 25-33, 1996.

Lands W., "Fish and Human Health", Academic Press, Inc. 1986.

Billman, et al., "Prevention of ischemia-induced ventricular fibrillation by ω-3 fatty acids", Proc. Natl. Acad. Sci. USA, vol. 91, May 1994: pp. 4427-430.

Ullmanns Encyklopädie der technischen Chemie, 4. Auglage, 1976, band 12, Seite 630: Herz-und Krieslaufmittel: g-Strpohantin.

Merck Manual, 13th Edition, 1997, pp. 403-416.

Merck Manual, 17th Edition, 1999, pp. 1740-1741.

Harrison's Principles of Internal Medicine, 15th Ed., pp. XIV, 1318-1322, 1374 (date unavailable).

A. Nordøy, et al., "n-3 polyunsaturated fatty acids and cardiovascular diseases", Lipids, vol. 36, 2001: pp. 127-129.

M.de Lorgeril, et al., Diet and medication for heart protection in secondary prevention of coronary heart disease. New concepts., Nutrition, metabolism, and cardiovasular diseases-NMCD, vol. 10 (4), Aug. 2000: pp. 216-222.

S.Sane, et al., "Eicosapentaenoic acid reduces pulmonary edema in endotoxemic rats," Journal of surgical research, vol. 93 (1). Sep. 2000: pp. 21-27.

W.S. Harris, et al., "safety and efficacy of Omacor in severe hypertriglyceridemia", Journal of cardiovascular risk, vol. 4(5-6), Dec. 1997: pp. 385-391.

G. Balestrieri, et al., "Fish oil supplementation in patients with heterozygous famillal hypercholesterolemia", Recenti progessi in medicinia, vol. 87 (3), Mar. 1996: pp. 102-105.

P. McLennan, et al., "The cardiovascular protective role of docosahexaenoic acid", European Journal of Pharmocology, 300 (1996) pp. 83-89.

D.W. Nilsen, et al., "Lipopolysaccharide induced monocyte thromboplastin synthese and coagulation responses in patients undergoing coronary bypass surgery after preoperative supplementation with n.3 fatty acids", Thrombosis and haemostasis, vol. 70(6), 1993 pp. 900-902.

M.S. Finkel, et al., "Bay K 8644 is a negative inotrope in the presence of arachiodnic acid but not eicosapentaenoic acid". Journal of cardiovascular pharmacology, vol. 20(4), 1992: pp. 563-571.

R.A.Siddiqui, et al. "Prevention of cardiac hypertrophy with omega-3 fatty acids: Potential cell signaling targets", Current Organic Chemistry, vol. 4(11), Dec. 2000: pp. 1145-1156.

E. Swahn, et al., "Omega-3 ethyl ester concentrate decreases total apolipoprotein CIII and increases an antithrombin III in postmyocardial infarction patients", Clinical Drug Investigation, vol. 15 (6), Jul. 1998: pp. 473-482.

K.Hayashi, et al., "Decreases in plasma lipid content and thrombotic activity by ethyl icosapentate purified from fish oil" Current Therapeutic Research-Clinical and Experimental, vol. 56 (1), Feb. 1995: pp. 24-31.

Simopoulos, Aretemis, "Nutritional Aspects of Fish,"Seafood from Producer to Consumer, Integrated Approach to Quality, Dev. Food Sci., 1997, pp. 589-607.

Das, U.N., "Free radicals, cytokines and nitric oxide in cardiac failure and myocardial infarction,"Molecular and Cellular Biochemistry, 2000, vol. 215, pp. 145-152.

Co-pending U.S. Appl. No. 09/869,333, filed Jul. 26, 2001.

\* cited by examiner

ESSENTIAL N-3 FATTY ACIDS IN CARDIAC INSUFFICIENCY AND HEART FAILURE THERAPY

CROSS-REFERENCE TO RELATED APPLICATIONS

This application is a continuation of U.S. patent application Ser. No. 10/451,623, filed Nov. 21, 2003, now abandoned, which is a National Stage of International Application No. PCT/EP02/00507, filed Jan. 16, 2002. The disclosures of the above applications are incorporated herein by reference.

The present invention belongs to the field of pharmaceutical chemistry and cardiovascular medicine and provides a method of prevention and management of cardiac insufficiency and heart failure: two heart diseases in which the second one is the result of the progressive evolution of the first one.

Cardiac insufficiency is a condition in which the heart pump function is inadequate to meet the bodily metabolic requirements. Depending on the different severity of the pump deficit, cardiac insufficiency may be symptom-free or clinically manifest.

Cardiac insufficiency could have various causes, e.g.:
disorders of myocardial function, which is the most frequent cause, due to a reduced contractility, but also to a loss of contractile tissue;
a volume load, due to disorders requiring the ventricle to expel more blood than the normal per minute;
a pressure load, due to disorders increasing the resistance to the outflow from the ventricles.

Heart failure is the result of the progressive evolution of cardiac insufficiency. Moreover, a broad spectrum of diseases could cause an impaired filling or emptying of heart chambers, such as: the diseases resulting from a monogenic (familial hypertrophic cardiomyopathy, mitochondral cardiomyopathies) or multigenic defect which are bound to environmental factors such as cigarette smoking, diet, physical exercise, secondary heart diseases. All these diseases take the "common end path" towards heart failure, which sees at first an impairment of the molecular mechanisms and then an impairment of the ventricular function and heart failure. Therefore, heart failure is a syndrome with a various etiology resulting from an anatomo-functional anomaly of the heart with inability in keeping a stroke adequate to the metabolic requirements of the tissues or maintaining the stroke volume by a high filling pressure.

Heart failure is characterized by clinical signs and symptoms secondary to the inadequate response to the body metabolic requirements. This condition could occur acutely or have a chronic course.

The pathophysiological interpretations of heart failure have had a remarkable evolution in time. This syndrome was considered as a pump deficiency associated with a renal dysfunction in years '50-'60, a pump dysfunction associated with an increase in peripheral resistance in years '70-'80 and is considered at present as a failure of the pump function associated with the neuro-hormonal activation with resulting hemodynamic impairments which take to a dysfunction of many organs and apparatuses.

The present drug therapy of cardiac "pump function" includes the use of drugs acting by various modes of action on different points of the etiopathogenesis of the diseases. We mention as an example: ACE-inhibitors (Angiotensin Converting Enzymes inhibitors), diuretics, non-digitalis positive inotropic drugs such as adrenergics and inhibitors of phosphodiesterase, arteriolar and venular vasodilators, e.g. hydralazine and isosorbide dinitrate, beta-blockers e.g. metoprolol and bisoprolol and digitalis derivatives, e.g. digotoxin.

Heart failure is at present one of the most important causes of morbidity and mortality in the industrialized countries, as clearly demonstrated by the present case-series: in USA 4.7 million persons have a congestive heart failure, with an incidence equal to 400,000 new cases a year.

The prevalence of chronic cardiac insufficiency rises from 8 cases of heart failure out of 1,000 subjects of age ranging from 50 to 59 years, to 66 cases out of 1,000 subjects between 80 and 89 years.

If we consider that about 35% of patients with heart failure are hospitalised at least once a year and that 80% of men and 65% of women die within 6 years, the social-health entity of the problem emerges in its full dramatic evidence.

Moreover, the incidence of heart failure seems to increase paradoxically with the reduction of death rate for myocardial infarction and for other cardiovascular diseases. The ageing of the population seems to be a contributing factor to amplify the relevance of the phenomenon.

Therefore, there is the need of a safe and convenient method of prevention and therapeutic treatment of cardiac insufficiency and heart failure, in particular in elderly patients, in order to restore (or to control) the usual pump function of the heart.

The present invention provides a method for the prevention and therapeutic treatment of cardiac insufficiency and heart failure in a patient in need of this treatment comprising the administration to such patient of a therapeutically effective amount of an essential fatty acid containing a mixture of (20:5ω3) eicosapentaenoic acid ethyl ester (EPA) and of (20:6ω3) docosahexaenoic acid ethyl ester (DHA), either alone or in combination with another therapeutic agent.

It is well known in the art that some essential fatty acids, in particular ω3 PUFA, contained for example in the fish oil, have a therapeutic effect in the prevention and therapy of cardiovascular disorders, e.g. in the prevention and treatment of atherothrombotic events and hyperlipidemia.

WO 89/11521 describes in particular an industrial process for the extraction of mixtures having a high content in polyunsaturated acids, also including EPA and DHA and their ethyl esters, from animal and/or vegetable oils. Mixtures of fatty acids, in particular EPA/DHA, obtained according to WO 89/11521, are indicated as particularly useful in the treatment of cardiovascular pathologies.

Therefore, object of the present invention is the use of an essential fatty acid containing a mixture of eicosapentaenoic acid ethyl ester (EPA) and docosahexaenoic acid ethyl ester (DHA) in the preparation of a medicament for the prevention and treatment of a heart disease chosen from cardiac insufficiency and heart failure, both chronic and acute.

For convenience of description, eicosapentaenoic acid ethyl ester and docosahexaenoic acid ethyl ester are mentioned here below respectively as "EPA" and "DHA".

An essential fatty acid, according to the invention, is preferably a fatty acid having a high content in EPA and DHA, for example with a content in EPA and DHA higher than 25% by weight, preferably from about 30% to about 100% by weight, in particular about 85%.

EPA is present in the EPA/DHA mixture preferably in a percentage ranging from 25% to about 45% by weight and DHA is present preferably in a percentage ranging from 55% to about 75% by weight.

At any rate, the most preferred ratio between EPA and DHA is about 0.6-1.1/1.3-1.8; in particular about 0.9/1.5.

An essential fatty acid according to the present invention can be obtained by known methods, e.g. as described in U.S. Pat. No. 5,656,667 and WO 89/11521.

Object of the present invention is also the use of an essential fatty acid containing a mixture of eicosapentaenoic acid ethyl ester (EPA) and docosahexaenoic acid ethyl ester (DHA) in the preparation of a medicament for the prevention and treatment of a heart disease chosen from cardiac insufficiency and heart failure, both chronic and acute, where the medicament is for combined therapy with another therapeutic agent.

The term "another therapeutic agent" means an additional single agent or two or more additional agents, preferably from 2 to 10, in particular from 2 to 6 according to physician's instructions, which may be administered in combination, namely either along or separately (substantially simultaneously or sequentially) with the essential fatty acid containing the mixture of EPA and DHA.

Examples of therapeutic agents for such a prophylaxis or combined therapy according to the invention are ACE-inhibitors, NEP-inhibitors, ACE/NEP-inhibitors, angiotensin II converting enzyme inhibitors, diuretics, positive inotropic drugs, phosphodiesterase inhibitors, arteriolar and venular vasodilators, beta-blockers and digitalis glycosides, or a mixture thereof.

NEP means degradation peptidase of atrial natriuretic peptide (ANP).

Examples of ACE-inhibitors are: captopril, enalapril, lisinopril, fosinopril, cilazapril, benazapril, perindopril, quinapril, ramipril, trandolapril and delapril, in particular cilazapril, captopril and enalapril.

Examples of ACE/NEP-inhibitors are: omapatrilat, sampatrilat and L-phenylalanine,N-[(2S)-2-(mercaptomethyl)-1-oxo-3-phenylpropyl]4-(2-thiazolyl) (compound Z13752A, a product of Zambon Company).

Examples of angiotensin II receptors antagonists (angiotensin II converting inhibitors) are: candesartan, valsartan and losartan.

Examples of diuretics are: hydrochlorothiazide, trichlormethiazide, chlorothiazide, chlortalidone, triamterene, clofenamide, furosemide, torasemide, ethacrynic acid, etozoline, spironolactone and amiloride, if the case in association with potassium sparing drugs, which are well known in the art, in particular furosemide and hydrochlorothiazide.

Examples of dopaminergic agents are dopamine and ibopamine.

Examples of phosphodiesterase inhibitors are: amrinone, milrinone, enoximone and bucladesine, in particular amrinone and enoximone.

Examples of arteriolar and venular vasodilators are: hydralazine and isosorbide dinitrate.

Examples of beta-blockers are: visoprolol, practotol, metoprolol, bucindol, carvedilol, atenolol, bisoprolol, celiprolol and nevibolol, in particular visoprolol, carvedilol and metoprolol.

Examples of digitalis glycoside agents are: acetyl digitoxin, acetyldigoxin, digitoxin, digoxin, lanatoside C, deslanoside, methyldigoxin and gitoformat, in particular digitoxin, digoxin, acetyldigoxin and metidigoxin.

Examples of positive inotropic agents are: pimobendan and vesnarinone, in particular pimobendan.

A further object of the invention is a method for preventing and treating a heart disease chosen from cardiac insufficiency and heart failure, both chronic and acute, comprising administering to a patient in need thereof a therapeutically effective amount of an unsaturated essential acid containing a mixture of eicosapentaenoic acid ethyl ester (EPA) and docosahexaenoic acid ethyl ester (DHA).

A further object of the invention is a method to prevent and treat a heart disease chosen from cardiac insufficiency and heart failure, both chronic and acute, comprising administering to a patient in need thereof a therapeutically effective amount of an essential fatty acid containing a mixture of eicosapentaenoic acid ethyl ester (EPA) and docosahexaenoic acid ethyl ester (DHA), in combination with another therapeutic agent.

The term "in combination" means that the essential fatty acid containing the mixture EPA+DHA and the other therapeutic agent are administered in such an amount and separated by such administration times as to produce a therapeutic effect.

The use of an essential fatty acid according to the invention is extremely useful in the prevention and treatment of cardiac insufficiency and heart failure both chronic and acute, in particular, in the elderly people, e.g. older than 60 years, in subjects with other further cardiopathic forms and, in particular, in subjects surviving a myocardial infarction, thanks to the fact that this is a well tolerated drug.

The amount of essential fatty acid to be administered to a patient, either as a single therapeutic agent or in combination with another therapeutic agent, depends on its EPA/DHA content. In particular, the amount of essential fatty acid having a EPA/DHA content of about 85%, to be administered to a patient, may vary from about 0.7 g to about 1.5 g daily. More specifically, the amount of essential fatty acid, with a EPA/DHA content of about 85% and an EPA/DHA ratio of about 0.9/1.5 is of about 1 g daily.

This amount of product may be administered in the form of several daily divided doses or preferably as a single dose, in order to reach the desired blood level. Of course, the clinician may vary the amount of product (or mixture with another therapeutic agent) to be administered, basing on the patient's conditions, age and weight.

The amount of additional therapeutic agent, when administered in combination with the essential fatty acid, is substantially the amount usually employed by the clinician in therapy. At any rate, the clinician may vary the amount of this additional drug (or mixture of additional drugs) basing on the patient's clinical picture.

The combined use of an essential fatty acid according to the invention and of another therapeutic agent produces a synergic or superadditive effect, namely an improvement of the patient's clinical picture surely greater than the one observed with the administration of the essential fatty acid or of the "other therapeutic agent" alone. Moreover, the greater therapeutic effect in the combined treatment is not accompanied by an increased toxicity.

Therefore, the present invention provides the clinician with a new method of therapeutic treatment effective for preventing and treating cardiac insufficiency and heart failure or at least improving the conditions of a patient suffering from such heart diseases or improving his/her quality of life. Indeed, on the basis of clinical markers, which are to-day useful to understand the various stages of cardiac insufficiency and progressive evolution towards an overt heart failure, the clinician can make use of the present invention and prevent or at least delay its evolution.

The pharmaceutical preparations according to the present invention can be prepared by methods well known in the art. A preferred route of administration is the oral one, but the physician may use to adopt other routes of administration e.g. the parenteral one.

The therapeutic agent for the combined therapy, according to the present invention, can be formulated as well known in the art.

The essential fatty acid can be formulated, for example, in the form of gelatin capsules as stated below.

Gelatin Capsules

According to the methods known from pharmaceutical technique, capsules are prepared with the following composition and containing 1 g of active ingredient (85% EPA-DHA) in each capsule.

| Formulation 1. | |
|---|---|
| EPA ethyl ester | 525 mg/capsule; |
| DHA ethyl ester | 315 mg/capsule; |
| d-alpha-tocopherol | 4 IU/capsule; |
| gelatin | 246 mg/capsule; |
| glycerol | 118 mg/capsule; |
| red iron oxide | 2.27 mg/capsule; |
| yellow iron oxide | 1.27 mg/capsule |

| Formulation 2. | |
|---|---|
| Ethyl esters of poly-unsaturated fatty acids | 1000 mg; |
| with content in ethyl esters of ω-3 poly-unsaturated acids (eicosapentaeonic EPA, docosahexaenoic DHA) | 850 mg; |
| d,l-alpha-tocopherol | 0.3 mg; |
| gelatin succinate | 233 mg |
| glycerol | 67 mg; |
| sodium p-hydroxybenzoate | 1.09 mg; |
| propyl sodium p-hydroxybenzoate | 0.54 mg. |

What is claimed is:

1. A method for treating a heart disease selected from the group consisting of chronic cardiac insufficiency and chronic heart failure, the method comprising administering to a patient in need thereof a therapeutically effective amount of essential fatty acids comprising a mixture of eicosapentaenoic acid ethyl ester (EPA) and docosahexaenoic acid ethyl ester (DHA) wherein the content of EPA+DHA in the mixture is higher than 25% by weight, as the sole therapeutic agent for the treatment of the chronic cardiac insufficiency or chronic heart failure.

2. The method according to claim 1, wherein the content of EPA+DHA in the mixture is from about 30% to about 100% by weight.

3. The method according to claim 1, wherein the content of EPA+DHA in the mixture is about 85% by weight.

4. The method according to claim 1, wherein the essential fatty acids are orally administered at a dose of from about 0.7 g to about 1.5 g daily.

5. The method according to claim 1, wherein the patient is a person older than 60 years.

6. A method for reducing acute heart failure events in a patient having heart disease, the method comprising administering to a patient having a heart disease selected from the group consisting of chronic cardiac insufficiency and chronic heart failure, essential fatty acids comprising a mixture of eicosapentaenoic acid ethyl ester (EPA) and docosahexaenoic acid ethyl ester (DHA) wherein the content of EPA+DHA in the mixture is higher than 25% by weight, in an amount effective to reduce acute heart failure events in the patient, wherein the essential fatty acids are the sole therapeutic agent for the treatment of the chronic cardiac insufficiency or chronic heart failure.

7. The method according to claim 6, wherein the content of EPA+DHA in the mixture is from about 30 to about 100% by weight.

8. The method according to claim 6, wherein the content of EPA+DHA in the mixture is about 85% by weight.

9. The method according to claim 6, wherein the essential fatty acids are administered orally at a dosage from about 0.7 g to about 1.5 g daily.

10. The method according to claim 6, wherein the patient is a person older than 60 years.

11. A method for reducing acute heart failure events in a patient having heart disease, the method comprising administering to a patient having a heart disease selected from the group consisting of chronic cardiac insufficiency and chronic heart failure, oral dosage forms comprising 1 g of oil containing ethyl esters of polyunsaturated fatty acids comprising omega-3 fatty acids comprising a mixture of eicosapentaenoic acid ethyl ester (EPA) and docosahexaenoic acid ethyl ester (DHA) wherein the content of EPA+DHA in the oil is greater than 25% by weight, in an amount effective to reduce acute heart failure events in the patient, wherein the essential fatty acids are the sole therapeutic agent for the treatment of the chronic cardiac insufficiency or chronic heart failure.

12. The method according to claim 11, wherein the content of EPA+DHA in the mixture is from about 30 to about 100% by weight.

13. The method according to claim 11, wherein the content of EPA+DHA in the mixture is about 85% by weight.

14. The method according to claim 11, wherein the patient is a person older than 60 years.

* * * * *